(12) United States Patent
Fought et al.

(10) Patent No.: US 9,788,540 B2
(45) Date of Patent: Oct. 17, 2017

(54) USE OF SUCCINATE DEHYDROGENASE INHIBITORS AND/OR RESPIRATORY CHAIN COMPLEX III INHIBITORS FOR IMPROVING THE RATIO OF HARMFUL TO BENEFICIAL MICROORGANISMS

(75) Inventors: Lorianne Fought, Kerman, CA (US); Herbert Young, Wake Forest, NC (US); George Musson, Raleigh, NC (US); Gilbert Labourdette, Paray le Monial (FR); Dominique Steiger, Düsseldorf (DE); Heiko Rieck, Burscheid (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 0 days.

(21) Appl. No.: 13/190,341

(22) Filed: Jul. 25, 2011

(65) Prior Publication Data
US 2012/0046323 A1    Feb. 23, 2012

Related U.S. Application Data

(60) Provisional application No. 61/367,525, filed on Jul. 26, 2010.

(30) Foreign Application Priority Data

Aug. 6, 2010   (EP) .................................... 10172128

(51) Int. Cl.
*A01N 37/50* (2006.01)
*A01N 43/40* (2006.01)

(52) U.S. Cl.
CPC ............. *A01N 37/50* (2013.01); *A01N 43/40* (2013.01)

(58) Field of Classification Search
None
See application file for complete search history.

(56) References Cited

U.S. PATENT DOCUMENTS

| | | | |
|---|---|---|---|
| 5,998,450 A | 12/1999 | Eicken et al. | |
| 6,696,487 B2 | 2/2004 | Gerusz et al. | |
| 7,329,633 B2 | 2/2008 | Dunkel et al. | |
| 7,538,073 B2 | 5/2009 | Elbe et al. | |
| 7,572,818 B2 | 8/2009 | Mansfield et al. | |
| 2008/0108686 A1 | 5/2008 | Gewehr et al. | |
| 2010/0324101 A1 | 12/2010 | Ebbinghaus et al. | |

FOREIGN PATENT DOCUMENTS

| | | |
|---|---|---|
| EP | 0 737 682 B1 | 1/2002 |
| EP | 1 559 320 A1 | 8/2005 |
| EP | 1 571 143 A1 | 9/2005 |
| EP | 2 100 506 A2 | 9/2009 |
| WO | WO 02/12172 A1 | 2/2002 |
| WO | WO 03/074491 A1 | 9/2003 |
| WO | WO 2004/035589 A1 | 4/2004 |
| WO | WO 2004/058723 A1 | 7/2004 |
| WO | WO 2006/015865 A1 | 2/2006 |
| WO | WO 2006/015866 A1 | 2/2006 |
| WO | WO 2008/148570 A1 | 12/2008 |
| WO | WO 2010/000612 A1 | 1/2010 |
| WO | WO 2010/086103 A2 | 8/2010 |
| WO | WO 2010/091803 A2 | 8/2010 |
| WO | WO 2010/149369 A1 | 12/2010 |

OTHER PUBLICATIONS

Avenot, H. F. and Michailides, T. J., "Progress in understanding molecular mechanisms and evolution of resistance to succinate dehydrogenase inhibiting(SDHI) fungicides in phytopathogenic fungi," *Crop Protection* 29:643-651, Elsevier Ltd., England (2010).
European Search Report for European Application No. EP 10 17 2128, European Patent Office, Munich, Germany, completed on Dec. 21, 2010.
Office Action mailed Apr. 10, 2013 in U.S. Appl. No. 12/786,663, inventors Ebbignhaus et al., filed May 25, 2010.
Office Action mailed Oct. 26, 2012 in U.S. Appl. No. 12/786,663, inventors Ebbignhaus et al., filed May 25, 2010.
Office Action mailed Apr. 24, 2012 in U.S. Appl. No. 12/786,663, inventors Ebbignhaus et al., filed May 25, 2010.

*Primary Examiner* — Mina Haghighatian
*Assistant Examiner* — Luke Karpinski
(74) *Attorney, Agent, or Firm* — McBee Moore Woodward & Vanik IP, LLC; Susan McBee; David Woodward (57) ABSTRACT

The present invention relates to the use of succinate dehydrogenase inhibitors and/or complex III inhibitors for controlling undesired fungal pathogens and simultaneously improving the ratio of harmful to beneficial microorganisms in crops and to a method for treating crops or parts of crops for controlling undesired fungal pathogens and simultaneously improving the ratio of harmful to beneficial microorganisms by treating the crops or parts of crops with a succinate dehydrogenase inhibitor and/or a complex III inhibitor.

17 Claims, 1 Drawing Sheet

USE OF SUCCINATE DEHYDROGENASE INHIBITORS AND/OR RESPIRATORY CHAIN COMPLEX III INHIBITORS FOR IMPROVING THE RATIO OF HARMFUL TO BENEFICIAL MICROORGANISMS

The present invention relates to the use of succinate dehydrogenase inhibitors and/or respiratory chain complex III inhibitors for controlling undesired fungal pathogens and simultaneously improving the ratio of harmful to beneficial microorganisms in crops and to a method for treating crops or parts of crops for controlling undesired fungal pathogens and simultaneously improving the ratio of harmful to beneficial microorganisms by treating the crops or parts of crops with a succinate dehydrogenase inhibitor and/or a complex III inhibitor.

For many years, microbiologists; plant pathologists and microbial ecologists have tended to differentiate and classify microorganisms as beneficial or harmful according to their functions and how they affect soil quality, plant growth and yield, plant health, root health, fruit quality and nutritional properties.

Beneficial microorganisms are those that can fix atmospheric nitrogen, decompose organic wastes and residues, detoxify pesticides, compete for limited nutrient availability with plant pathogens (niche exclusion) supplant or suppress above ground and/or and soil-borne plant diseases, suppress or kill insects and/or nematodes, enhance nutrient cycling, and produce bioactive compounds such as vitamins, hormones and enzymes that stimulate plant growth.

Live microorganisms thought to be healthy for the host organism are also known as "Probiotics". According to the currently adopted definition by FAO/WHO, probiotics are: "Live microorganisms which when administered in adequate amounts confer a health benefit on the host". Lactic acid bacteria (LAB) and bifidobacteria are the most common types of microbes used as probiotics; but certain yeasts and bacilli may also be helpful. Probiotics are commonly consumed as part of fermented foods with specially added active live cultures; such as in yogurt, soy yogurt, or as dietary supplements.

Harmful microorganisms, also called "pathogens", are those that can cause plant diseases of fruit, roots, foliage and other plant parts, immobilize nutrients, and produce toxic and putrescent substances that adversely affect plant growth, health and yields.

Accordingly, there is a strong need for active ingredients which guarantee—on the one hand—an effective control of harmful microorganisms and which—on the other hand—do not affect the activities of beneficial microorganisms. It would be desirable if such active ingredients even would increase the quantity of beneficial microorganisms.

It has been surprisingly found by the present inventors that succinate dehydrogenase inhibitors and/or respiratory chain complex III inhibitors, in particular fluopyram, effectively control the presence of a large number of harmful or at least undesired fungal pathogens, while the presence of beneficial microorganisms on the treated crop is at least not impaired or more preferably even significantly increased. Consequently, the treatment of the crops according to the invention leads to an improved ratio of harmful to beneficial microorganisms.

Thus, the present invention relates to the use of succinate dehydrogenase inhibitors and/or respiratory chain complex III inhibitors for controlling undesired fungal pathogens without impairing the content of beneficial microorganisms in crops and more preferably to a simultaneous improvement of the ratio of harmful to beneficial microorganisms.

In conjunction with the present invention "controlling" denotes a significant reduction of pathogens in comparison to the untreated crop, more preferably the infestation is essentially diminished (50-79%), most preferably the infestation is totally suppressed (80-100%).

In conjunction with the present invention "not impaired" means that neither the content nor the activity of the beneficial microorganisms after the treatment with the succinate dehydrogenase inhibitor and/or the complex III inhibitor is decreased.

In conjunction with the present invention "increasing the content of beneficial microorganisms" means that after the treatment with the succinate dehydrogenase inhibitor and/or the complex III inhibitor the content of the beneficial microorganism is higher than before treatment. Preferably the content of the beneficial microorganism is as twice as high as before treatment with the succinate dehydrogenase inhibitor and/or the complex III inhibitor. More preferably the content of the beneficial microorganism is tenfold increased after treatment with the succinate dehydrogenase inhibitor and/or the complex III inhibitor.

The phrase "improved ratio of harmful to beneficial microorganisms" denotes that the content of harmful microorganisms is decreased while the content of beneficial microorganisms remains constant or preferably is increased.

In the context of the present invention, succinate dehydrogenase inhibitors are all active compounds having an inhibiting action on the enzyme succinate dehydrogenase in the mitochondrial respiratory chain. In a preferred embodiment of the present invention, the succinate dehydrogenase inhibitors are selected from the group consisting of fluopyram, isopyrazam, boscalid, penthiopyrad, penflufen, sedaxane, fluxapyroxad, bixafen and 3-difluoromethyl-1-methyl-1H-pyrazole-4-carboxylic acid [2-(2,4-dichlorophenyl)-2-methoxy-1-methyl-ethyl]-amide and also from mixtures of these compounds. In a particularly preferred embodiment of the present invention, the succinate dehydrogenase inhibitor is fluopyram.

Bixafen of the chemical name N-(3',4'-dichloro-5-fluoro-1,1'-biphenyl-2-yl)-3-(difluoromethyl)-1-methyl-1H-pyrazole-4-carboxamide and processes suitable for its preparation from commercially available starting materials are described in WO 03/070705.

Penflufen of the chemical name N-[2-(1,3-dimethylbutyl)phenyl]-5-fluoro-1,3-dimethyl-1H-pyrazole-4-carboxamide and processes suitable for its preparation from commercially available starting materials are described in WO 03/010149.

Fluopyram of the chemical name N-{[3-chloro-5-(trifluoromethyl)-2-pyridinyl]ethyl}-2-(trifluoromethyl) benzamide, and processes suitable for its preparation from commercially available starting materials are described in EP-A-1 389 614.

Sedaxane is a mixture comprising the two cis-isomers of 2'-[(1RS,2RS)-1,1'-bicycloprop-2-yl]-3-(difluoro-methyl)-1-methylpyrazole-4-carboxanilide and the two trans-isomers of 2'-[(1RS,2SR)-1,1'-bicycloprop-2-yl]-3-(difluoromethyl)-1-methylpyrazole-4-carboxanilide. Sedaxane and processes suitable for its preparation from commercially available starting materials are described in WO 03/074491, WO 2006/015865 and WO 2006/015866.

Isopyrazam is a mixture comprising the two syn-isomers of 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and the two anti-isomers of 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide. Isopyrazam and processes suitable for its preparation from commercially available starting materials are described in WO 2004/035589.

Penthiopyrad of the chemical name (RS)—N-[2-(1,3-dimethylbutyl)-3-thienyl]-1-methyl-3-(trifluoromethyl)pyrazole-4-carboxamide and processes suitable for its preparation from commercially available starting materials are described in EP-A-0 737 682.

Boscalid of the chemical name 2-chloro-N-(4'-chlorobiphenyl-2-yl)nicotinamide and processes suitable for its preparation from commercially available starting materials are described in DE-A 195 31 813.

Fluxapyroxad of the chemical name 3-(difluoromethyl)-1-methyl-N-(3',4',5'-trifluoro-biphenyl-2-yl)-1H-pyrazole-4-carboxamide and processes suitable for its preparation from commercially available starting materials are described in WO 2005/123690.

3-Difluoromethyl-1-methyl-1H-pyrazole-4-carboxylic acid [2-(2,4-dichlorophenyl)-2-methoxy-1-methyl-ethyl]-amide usually is a mixture of 4 different stereo isomers. Processes suitable for its preparation from commercially available starting materials are described in WO 2008/148570. The different stereo isomers (+)-3-difluoromethyl-1-methy 1-1H-pyrazole-4-carboxylic acid [(1R,2S)-2-(2,4-dichlorophenyl)-2-methoxy-1-methyl-ethyl]-amide, (−)-3-difluoromethyl-1-methyl-1H-pyrazole-4-carboxylic acid [(1S,2R)-2-(2,4-dichlorophenyl)-2-methoxy-1-methyl-ethyl]-amide; (+3-difluoromethyl-1-methy 1-1H-pyrazole-4-carboxylic acid[(1R,2R)-2-(2,4-dichlorophenyl)-2-methoxy-1-methyl-ethyl]-amide and (+)-3-difluoromethyl-1-methyl-1H-pyrazole-4-carboxylic acid [(1S,2S)-2-(2,4-dichlorophenyl)-2-methoxy-1-methyl-ethyl]-amide can be separated, for example by HPLC, using a chiral stationary phase column, as described in WO 2010/000612.

Inhibitors of the respiratory chain at complex III, also referred herein to "complex III inhibitors", which can be used in accordance with the present invention are selected from the group consisting of for example (3.1) amisulbrom (348635-87-0), (3.2) azoxystrobin (131860-33-8), (3.3) cyazofamid (120116-88-3), (3.4) dimoxystrobin (141600-52-4), (3.5) enestroburin (238410-11-2) (known from WO 2004/058723), (3.6) famoxadone (131807-57-3) (known from WO 2004/058723), (3.7) fenamidone (161326-34-7) (known from WO 2004/058723), (3.8) fluoxastrobin (361377-29-9) (known from WO 2004/058723), (3.9) kresoxim-methyl (143390-89-0) (known from WO 2004/058723), (3.10) metominostrobin (133408-50-1) (known from WO 2004/058723), (3.11) orysastrobin (189892-69-1) (known from WO 2004/058723), (3.12) picoxystrobin (117428-22-5) (known from WO 2004/058723), (3.13) pyraclostrobin (175013-18-0) (known from WO 2004/058723), (3.14) pyrametostrobin (915410-70-7) (known from WO 2004/058723), (3.15), pyraoxystrobin (862588-11-2) (known from WO 2004/058723), (3.16) pyribencarb (799247-52-2) (known from WO 2004/058723), (3.17) trifloxystrobin (141517-21-7) (known from WO 2004/058723), (3.18) (2E)-2-(2-{[6-(3-chloro-2-methyl phenoxy)-5-fluoropyrimidin-4-yl]oxy}phenyl)-2-(methoxyimino)-N-methyl-ethanamide (known from WO 2004/058723), (3.19) (2E)-2-(methoxyimino)-N-methyl-2-(2-{[({(1E)-1-[3-(trifluoromethyl)phenyl]ethylidene}amino)oxy]methyl}phenyl)ethanamide (known from WO 2004/058723) and salts thereof, (3.20) (2E)-2-(methoxyimino)-N-methyl-2-{2-[(E)-({1-[3-(trifluoromethyl)phenyl]ethoxy}imino)methyl]phenyl}ethanamide (158169-73-4), (3.21) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.22) (2E)-2-{2-[({[(2E,3E)-4-(2,6-dichlorophenyl)but-3-en-2-ylidene]amino}oxy)methyl]-phenyl}-2-(methoxyimino)-N-methylethanamide, (3.23) 2-chloro-N-(1,1,3-trimethyl-2,3-dihydro-1H-inden-4-yl)pyridine-3-carboxamide (119899-14-8), (3.24) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.27) 2-{2-[(2,5-dimethylphenoxy)methyl]phenyl}-2-methoxy-N-methylacetamide (173662-97-0), (3.28) (2R)-2-{2-[(2,5-dimethylphenoxy)methyl]phenyl}-2-methoxy-N-methylacetamide (394657-24-0) and salts thereof.

In a preferred embodiment of the invention the complex III inhibitor is a strobilurine selected from the group consisting of (3.1) amisulbrom (348635-87-0), (3.2) azoxystrobin (131860-33-8), (3.4) dimoxystrobin (141600-52-4), (3.5) enestroburin (238410-11-2) (known from WO 2004/058723), (3.8) fluoxastrobin (361377-29-9) (known from WO 2004/058723), (3.9) kresoxim-methyl (143390-89-0) (known from WO 2004/058723), (3.10) metominostrobin (133408-50-1) (known from WO 2004/058723), (3.11) orysastrobin (189892-69-1) (known from WO 2004/058723), (3.12) picoxystrobin (117428-22-5) (known from WO 2004/058723), (3.13) pyraclostrobin (175013-18-0) (known from WO 2004/058723), (3.14) pyrametostrobin (915410-70-7) (known from WO 2004/058723), (3.15), pyraoxystrobin (862588-11-2) (known from WO 2004/058723), (3.16) pyribencarb (799247-52-2) (known from WO 2004/058723), (3.17) trifloxystrobin (141517-21-7) (known from WO 2004/058723), (3.18) (2E)-2-(2-{[6-(3-chloro-2-methylphenoxy)-5-fluoropyrimidin-4-yl]oxy}phenyl)-2-(methoxyimino)-N-methyl-ethanamide (known from WO 2004/058723), (3.19) (2E)-2-(methoxyimino)-N-methyl-2-(2-{[({(1E)-1-[3-(trifluoromethyl)phenyl]ethylidene}amino)oxy]methyl}phenyl)ethanamide (known from WO 2004/058723) and salts thereof, (3.20) (2E)-2-(methoxyimino)-N-methyl-2-{2-[(E)-({1-[3-(trifluoromethyl)phenyl]-ethoxy}imino)methyl]phenyl}ethanamide (158169-73-4), (3.21) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.22) (2E)-2-{2-[({[(2E,3E)-4-(2,6-dichlorophenyl)but-3-en-2-ylidene]amino}oxy)methyl]-phenyl}-2-(methoxyimino)-N-methylethanamide, (3.23) 2-chloro-N-(1,1,3-trimethyl-2,3-dihydro-1H-inden-4-yl)pyridine-3-carboxamide (119899-14-8), (3.24) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.27) 2-{2-[(2,5-dimethylphenoxy)methyl]phenyl}-2-methoxy-N-methylacetamide (173662-97-0), (3.28) (2R)-2-{2-[(2,5-dimethylphenoxy)methyl]phenyl}-2-methoxy-N-methylacetamide (394657-24-0) and salts thereof.

Most preferably, trifloxystrobine or fluopyram or a combination of both is used.

As a non-exhaustive enumeration, examples of beneficial microorganisms are selected from the group consisting of pink yeast, white yeast, yellow yeast, *Bacillus* spp., *Epicoccum* spp., white bacteria, yellow bacteria, black bacteria, *Paecilomyces* spp., and *Ulocladium* spp., preferably from

*Paecilomyces* spp., *Ulocladium* spp., white and yellow yeasts and white and yellow bacteria most preferably of yellow bacteria As a non-exhaustive enumeration, examples of harmful microorganisms are selected from the group consisting of *Botrytis* spp, *Rhizopus* spp, *Penicillium* spp., *Cladosporium* spp., *Aspergillus niger, Aspergillus flavus, Aspergillus* spp., *Alternaria* spp., *Fusarium* spp., *Aerobasidium* spp. Powdery Mildew Diseases such as *Blumeria* diseases caused for example by *Blumeria graminis*.
*Podosphaera* diseases caused for example by *Podosphaera leucotricha*
*Sphaerotheca* diseases caused for example by *Sphaerotheca fuliginea*
*Uncinula* diseases caused for example by *Uncinula necator*
   Rust Diseases such as
*Gymnosporangium* diseases caused for example by *Gymnosporangium sabinae*
*Hemileia* diseases caused for example by *Hemileia vastatrix*
*Phakopsora* diseases caused for example by *Phakopsora pachyrhizi* and *Phakopsora meibomiae*
*Puccinia* diseases caused for example by *Puccinia recondite*, and *Puccinia triticina*;
*Uromyces* diseases caused for example by *Uromyces appendiculatus*
Oomycete Diseases such as
*Bremia* diseases caused for example by *Bremia lactucae*
*Peronospora* diseases caused for example by *Peronospora pisi* and *Peronospora brassicae*
*Phytophthora* diseases caused for example by *Phytophthora infestans*
*Plasmopara* diseases caused for example by *Plasmopara viticola*
*Pseudoperonospora* diseases caused for example by *Pseudoperonospora humuli* and *Pseudoperonospora cubensis*
*Pythium* diseases caused for example by *Pythium ultimum*
   Leafspot, Leaf blotch and Leaf Blight Diseases such as
*Alternaria* diseases caused for example by *Alternaria solani*
*Cercospora* diseases caused for example by *Cercospora beticola*
*Cladiosporium* diseases caused for example by *Cladiosporium cucumerinum*
*Cochliobolus* diseases caused for example by *Cochliobolus sativus*
(Conidiaform: *Drechslera*, Syn: *Helminthosporium*);
*Colletotrichum* diseases caused for example by *Colletotrichum lindemuthianum*
*Cycloconium* diseases caused for example by *Cycloconium oleaginum*
*Diaporthe* diseases caused for example by *Diaporthe citri*
*Elsinoe* diseases caused for example by *Elsinoe fawcettii*
*Gloeosporium* diseases caused for example by *Gloeosporium laeticolor*
*Glomerella* diseases caused for example by *Glomerella cingulata*
*Guignardia* diseases caused for example by *Guignardia bidwellii*
*Leptosphaeria* diseases caused for example by *Leptosphaeria maculans*
*Magnaporthe* diseases caused for example by *Magnaporthe grisea*
*Mycosphaerella* diseases caused for example by *Mycosphaerella graminicola* and *Mycosphaerella fijiensis*
*Phaeosphaeria* diseases caused for example by *Phaeosphaeria nodorum*
*Pyrenophora* diseases caused for example by *Pyrenophora teres*
*Ramularia* diseases caused for example by *Ramularia collocygni*
*Rhynchosporium* diseases caused for example by *Rhynchosporium secalis*
*Septoria* diseases caused for example by *Septoria apii*;
*Typhula* diseases caused for example by *Thyphula incarnata*
*Venturia* diseases caused for example by *Venturia inaequalis*
   Root- and Stem Diseases such as
*Corticium* diseases caused for example by *Corticium graminearum*
*Fusarium* diseases caused for example by *Fusarium oxysporum*
*Gaeumannomyces* diseases caused for example by *Gaeumannomyces graminis*
*Rhizoctonia* diseases caused for example by *Rhizoctonia solani*
*Oculimacula (Tapesia)* diseases caused for example by *Oculimacula Tapesia acuformis*
*Thielaviopsis* diseases caused for example by *Thielaviopsis basicola*
   Ear and Panicle Diseases including Maize cob such as
*Alternaria* diseases caused for example by *Alternaria* spp.
*Aspergillus* diseases caused for example by *Aspergillus flavus*
*Cladosporium* diseases caused for example by *Cladosporium cladosporioides*
*Claviceps* diseases caused for example by *Claviceps purpurea*
*Fusarium* diseases caused for example by *Fusarium culmorum*
*Gibberella* diseases caused for example by *Gibberella zeae*
*Monographella* diseases caused for example by *Monographella nivalis*
   Smut- and Bunt Diseases such as
*Sphacelotheca* diseases caused for example by *Sphacelotheca reiliana*
*Tilletia* diseases caused for example by *Tilletia caries*
*Urocystis* diseases *Urocystis occulta*
*Ustilago* diseases caused for example by *Ustilago nuda*;
   Fruit Rot and Mould Diseases such as
*Aspergillus* diseases caused for example by *Aspergillus flavus*
*Botrytis* diseases caused for example by *Botrytis cinerea*
*Penicillium* diseases caused for example by *Penicillium expansum* and *Penicillium purpurogenum*
*Sclerotinia* diseases caused for example by *Sclerotinia sclerotiorum*;
*Verticillium* diseases caused for example by *Verticillium alboatrum*
   Seed- and Soilborne Decay, Mould, Wilt, Rot and Damping-off diseases
*Fusarium* diseases caused for example by *Fusarium culmorum*
*Phytophthora* diseases caused for example by *Phytophthora cactorum*
*Pythium* diseases caused for example by *Pythium ultimum*
*Rhizoctonia* diseases caused for example by *Rhizoctonia solani*
*Sclerotium* diseases caused for example by *Sclerotium rolfsii*
   Canker, Broom and Dieback Diseases such as
*Nectria* diseases caused for example by *Nectria galligena*
   Blight Diseases such as
*Monilinia* diseases caused for example by *Monilinia laxa*
   Leaf Blister or Leaf Curl Diseases including deformation of blooms and fruits such as
*Taphrina* diseases caused for example by *Taphrina deformans*

Decline Diseases of Wooden Plants such as
*Esca* disease caused for example by *Phaeomoniella clamydospora* and *Phaeoacremonium aleophilum* and *Fomitiporia mediterranea*
Diseases of Flowers and Seeds such as
*Botrytis* diseases caused for example by *Botrytis cinema*
Diseases of Tubers such as
*Rhizoctonia* diseases caused for example by *Rhizoctonia solani*
*Helminthosporium* diseases caused for example by *Helminthosporium solani*
Diseases caused by Bacterial Organisms such as *Xanthomanas* species for example *Xanthomonas campestris* pv. *Oryzae*
*Pseudomonas* species for example *Pseudomonas syringae* pv. *Lachrymans*
*Erwinia* species for example *Erwinia amylovora*.

*Aspergillus flavus*, most strains of *Aspergillus parasiticus*, *Aspergillus nomius*, *Aspergillus bombycis*, *Aspergillus pseudotamarii*, *Aspergillus ochraceoroseus*, *Aspergillus rambelli*, *Emericella astellata*, *Emericella venezuelensis*, *Bipolaris* spp., *Chaetomium* spp., *Farrowia* spp., and *Monocillium* spp., in particular *Aspergillus flavus* and *Aspergillus parasiticus*, *Fusarium graminearum*, *Fusarium culmorum*, *Fusarium cerealis Fusarium acuminatum*, *Fusarium crookwellense*, *Fusarium verticillioides*, *Fusarium culmorum*, *Fusarium avenaceum*, *Fusarium equiseti*, *Fusarium moniliforme*, *Fusarium graminearum* (*Gibberella zeae*), *Fusarium lateritium*, *Fusarium poae*, *Fusarium sambucinum* (*G. pulicaris*), *Fusarium proliferatum*, *Fusarium subglutinans*, *Fusarium sporotrichioides* and other *Fusarium* species.

In general, the use/method according to the present invention can be applied to any kind of crops/plants.

By plant parts is meant all above ground and below ground parts and organs of plants such as shoot, leaf, flower, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners, tubers, grains, and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa*, *B. juncea* (e.g. mustard) and *Brassica* carinata, rice, wheat, sugarbeet, sugarcane, oats, lye, barley, millet, triticale, flax, vine and various fruits and vegetables of various botanical taxa such as *Rosaceae* spp. (for instance pip fruit such as apples and pears, but also stone fruit such as apricots, cherries, almonds and peaches, berry fruits such as strawberries), *Ribesioidae* spp., *Juglandaceae* spp., *Betulaceae* spp., *Anacardiaceae* spp., *Fagaceae* spp., *Moraceae* spp., *Oleaceae* spp., *Actinidaceae* spp., *Lauraceae* spp., *Musaceae* spp. (for instance banana trees and plantings), *Rubiaceae* spp. (for instance coffee), *Theaceae* spp., *Sterculiceae* spp., *Rutaceae* spp. (for instance lemons, oranges and grapefruit); *Solanaceae* spp. (for instance tomatoes, potatoes, peppers, eggplant), *Liliaceae* spp., *Compositiae* spp. (for instance lettuce, artichoke and chicory—including root chicory, endive or common chicory), *Umbelliferae* spp. (for instance carrot, parsley, celery and celeriac), *Cucurbitaceae* spp. (for instance cucumber—including pickling cucumber, squash, watermelon, gourds and melons), *Alliaceae* spp. (for instance onions and leek), *Cruciferae* spp. (for instance white cabbage, red cabbage, broccoli, cauliflower, brussel sprouts, pak choi, kohlrabi, radish, horseradish, cress, Chinese cabbage), *Leguminosae* spp. (for instance peanuts, peas and beans beans—such as climbing beans and broad beans), *Chenopodiaceae* spp. (for instance mangold, spinach beet, spinach, beetroots), *Asteraceae* spp. (for instance sunflower), *Brassicaceae* spp. (for instance white cabbage, red cabbage, brokkoli, cauliflower, brussel sprouts, pak choi, kohlrabi, radish as well as canola, rapeseed, mustard, horseradish, cress), (*Cruciferae* spp. (for instance colza), *Fabacae* spp. (for instance peanuts and beans), *Papilionaceae* spp. (for instance soybean), *Solanaceae* spp. (for instance potatoes), *Malvaceae* (for instance okra), *Asparagaceae* (for instance asparagus); horticultural and forest crops; ornamental plants; as well as genetically modified homologues of these crops.

According to the invention all cereal, nut, fruit and spice plants are comprised, in particular cereals like all wheat species, rye, barley, triticale, rice, sorghum, oats, millets, quinoa, buckwheat, fonio, amaranth, teff and durum; in particular fruits of various botanical taxa such as *Rosaceae* spp. (for instance pip fruit such as apples and pears, but also stone fruit such as apricots, cherries, almonds and peaches, berry fruits such as strawberries), *Vitis* spp. (for instance *Vitis vinifera*: grape vine, raisins), *Manihoteae* spp. (for instance *Manihot esculenta*, manioc), *Theobroma* spp. (for instance *Theobroma cacao*: cocoa), *Ribesioidae* spp., *Juglandaceae* spp., *Betulaceae* spp., *Anacardiaceae* spp., *Fagaceae* spp., *Moraceae* spp., *Oleaceae* spp., *Actinidaceae* spp., *Lauraceae* spp., *Musaceae* spp. (for instance banana trees and plantings), *Rubiaceae* spp. (for instance coffee), *Theaceae* spp., *Sterculiceae* spp., *Rutaceae* spp. (for instance lemons, oranges and grapefruit); *Solanaceae* spp. (for instance tomatoes, potatoes, peppers, eggplant), *Liliaceae* spp.; in particular nuts of various botanical taxa such as peanuts, *Juglandaceae* spp. (Walnut, Persian Walnut (*Juglans regia*), Butternut (*Juglans*), Hickory, Shagbark Hickory, Pecan (*Carya*), Wingnut (*Pterocarya*)), *Fagaceae* spp. (Chestnut (*Castanea*), Chestnuts, including Chinese Chestnut, Malabar chestnut, Sweet Chestnut, Beech (*Fagus*), Oak (*Quercus*), Stone-oak, Tanoak (*Lithocarpus*)); *Betulaceae* spp. (Alder (*Alnus*), Birch (*Betula*), Hazel, Filbert (*Corylus*), Hornbeam), *Leguminosae* spp. (for instance peanuts, peas and beans beans—such as climbing beans and broad beans), *Asteraceae* spp. (for instance sunflower seed), Almond, Beech, Butternut, Brazil nut, Candlenut, Cashew, Colocynth, Cotton seed, Cucurbita ficifolia, Filbert, Indian Beech or Pongam Tree, Kola nut, Lotus seed, Macadamia, Mamoncillo, Maya nut, Mongongo, Oak acorns, Ogbono nut, Paradise nut, Pili nut, Pine nut, Pistacchio, Pumpkin seed, water Caltrop; soybeans (*Glycine* spp., *Glycine max*); in particular spices like Ajwain (*Trachyspermum ammi*), Allspice (*Pimenta dioica*), Alkanet (*Anchusa arvensis*), Amchur—mango powder (*Mangifera*), Angelica (*Angelica archangelica*), Anise (*Pimpinella anisum*), Aniseed myrtle (*Syzygium anisatum*), Annatto (*Bixa orellana* L.), Apple mint (*Mentha suaveolens*), *Artemisia vulgaris*/Mugwort, Asafoetida (*Ferula assafoetida*), Berberis, Banana, Basil (*Ocimum basilicum*), Bay leaves, Bistort (*Persicaria bistorta*"), Black cardamom, Black cumin, Blackcurrant, Black limes, Bladder wrack (*Fucus vesiculosus*), Blue Cohosh, Blue-leaved Mallee (*Eucalyptus polybractea*), Bog Labrador Tea (*Rhododendron groenlandicum*), Boldo (*Peumus boldus*), Bolivian Coriander (*Porophyllum ruderale*), Borage (*Borago officinalis*), Calamus, Calendula, Calumba (*Jateorhiza calumba*), Chamomile, Candle nut, Cannabis, Caper (*Capparis spinosa*), Caraway, Cardamom, Carob Pod, *Cassia*, *Casuarina*, Catnip, Cat's Claw, Catsear, Cayenne pepper, *Celastrus Paniculatus*—Herb, Celery salt, Celery seed, Centaury, Chervil (*Anthriscus cerefolium*), Chickweed, Chicory, Chile pepper, Chili powder, Cinchona, Chives (*Allium schoenoprasum*), Cicely (*Myrrhis odorata*), Cilantro (see Coriander) (*Coriandrum sativum*), Cinnamon (and *Cassia*), Cinnamon Myrtle (*Backhousia myrtifolia*), Clary, Cleavers, Clover, Cloves, Coffee, Coltsfoot, Comfrey, Common Rue, Condurango, Coptis, Coriander, Costmary (*Tanacetum balsamita*), Couchgrass, Cow Parsley (*Anthriscus sylvestris*), Cowslip, Cramp Bark (*Viburnum opulus*), Cress, Cuban Oregano (*Plectranthus amboinicus*), Cudweed, Cumin, Curry leaf (*Murraya koenigii*), Damiana (*Turnera aphrodisiaca, T. diffusa*), Dandelion (*Taraxacum officinale*), Demulcent, Devil's claw (*Harpagophytum procumbens*), Dill seed, Dill (*Anethum graveolens*), Dorrigo Pepper (*Tasmannia stipitata*), Echinacea *Echinopanax Elatum*, Edelweiss, Elderberry, Elderflower, Elecampane, *Eleutherococcus senticosus*, Emmenagogue, Epazote (*Chenopodium ambrosioides*), Ephedra *Eryngium foetidum*, *Eucalyptus*, Fennel (*Foeniculum vulgare*), Fenugreek, Feverfew, Figwort, File powder, Five-spice powder (Chinese), Fo-ti-tieng, Fumitory, Galangal, Garam masala, Garden cress, Garlic chives, Garlic, Ginger (*Zingiber officinale*), *Ginkgo biloba*, Ginseng, Ginseng, Siberian (*Eleutherococcus senticosus*), Goat's Rue (*Galega officinalis*), Goada masala, Golden Rod, Golden Seal, Gotu Kola, Grains of paradise (*Aframomum melegueta*), Grains of Selim (*Xylopia aethiopica*), Grape seed extract, Green tea, Ground Ivy, Guaco, Gypsywort, Hawthorn (*Crataegus sanguinea*), Hawthorne Tree, Hemp, Herbes de Provence, Hibiscus, Holly, Holy Thistle, Hops, Horehound, Horseradish, Horsetail (*Equisetum telmateia*), Hyssop (*Hyssopus officinalis*), Jalap, Jasmine, Jiaogulan (*Gynostemma pentaphyllum*), Joe Pye weed (Gravelroot), John the Conqueror, Juniper, Kaffir Lime Leaves (*Citrus hystrix, C. papedia*), Kaala masala, Knotweed, Kokam, Labrador tea, Lady's Bedstraw, Lady's Mantle, Land cress, Lavender (*Lavandula* spp.), Ledum, Lemon Balm (*Melissa Officinalis*), Lemon basil, Lemongrass (*Cymbopogon citratus, C. flexuosus*, and other species), Lemon Ironbark (*Eucalyptus staigeriana*), Lemon mint, Lemon Myrtle (*Backhousia citriodora*), Lemon Thyme, Lemon verbena (*Lippia citriodora*), Licorice—adaptogen, Lime Flower, *Limnophila aromatica*, Lingzhi, Linseed, Liquorice, Long pepper, Lovage (*Levisticum officinale*), *Luohanguo*, Mace, Mahlab, Malabathrum, Manchurian Thorn Tree (*Aralia manchurica*)]], Mandrake, Marjoram (*Origanum majorana*), *Marrubium vulgare*, Marsh Labrador Tea, Marshmallow, Mastic, Meadowsweet, Mei Yen, Melegueta pepper (*Aframomum melegueta*), Mint (*Mentha* spp.), Milk thistle (*Silybum*), Bergamot (*Monarda didyma*), Motherwort, Mountain Skullcap, Mullein (*Verbascum thapsus*), Mustard, Mustard seed, *Nashia inaguensis*, Neem, *Nepeta*, Nettle, *Nigella sativa*, Nigella (Kolanji, Black caraway), Noni, Nutmeg (and Mace) Marijuana, Oenothera (*Oenothera biennis* et al), Olida (*Eucalyptus olida*), Oregano (*Origanum vulgare, O. heracleoticum*, and other species), Orris root, Osmorhiza, Olive Leaf (used in tea and as herbal supplement), *Panax quinquefolius*, Pandan leaf, Paprika, Parsley (*Petroselinum crispum*), Passion Flower, Patchouli, Pennyroyal, Pepper (black, white, and green), Peppermint, Peppermint Gum (*Eucalyptus dives*), *Perilla*, Plantain, Pomegranate, Ponch phoran, Poppy seed, Primrose (*Primula*)—candied flowers, tea, Psyllium, Purslane, Quassia, Quatre spices, Ramsons, Ras el-hanout, Raspberry (leaves), Reishi, Restharrow, Rhodiola rosea, Riberry (*Syzygium luehmannii*), Rocket/Arugula, Roman chamomile, Rooibos, Rosehips, Rosemary (*Rosmarinus officinalis*), Rowan Berries, Rue, Safflower, Saffron, Sage (*Salvia officinalis*), Saigon Cinnamon, St John's Wort, Salad Bumet (*Sanguisorba minor* or *Poterium sanguisorba*), Salvia, Sichuan Pepper (*Sansho*), Sassafras, Savory (*Satureja hortensis, S. Montana*), Schisandra (*Schisandra chinensis*), Scutellaria costaricana, Senna (herb), *Senna obtusifolia*, Sesame seed, Sheep Sorrel, Shepherd's Purse, Sialagogue, Siberian Chaga, Siberian ginseng (*Eleutherococcus senticosus*), Siraitia grosvenorii (*luohanguo*), Skullcap, Sloe Berries, Smudge Stick, Sonchus, Sorrel (*Rumex* spp.), Southernwood, Spearmint, Speedwell, Squill, Star anise, Stevia, Strawberry Leaves, Suma (*Pfaffia paniculata*), Sumac, Summer savory, *Sutherlandia frutescens*, Sweet grass, Sweet cicely (*Myrrhis odorata*), Sweet woodruff, Szechuan pepper (*Xanthoxylum piperitum*), Tacamahac, Tamarind, Tandoori masala, Tansy, Tarragon (*Artemisia dracunculus*), Tea, *Teucrium polium*, That basil, Thistle, Thyme, Toor Dall, Tormentil, Tribulus terrestris, Tulsi (*Ocimum tenuiflorum*), Turmeric (*Curcuma longa*), Uva Ursi also known as Bearberry, Vanilla (*Vanilla planifolia*), Vasaka, Vervain, Vetiver, Vietnamese Coriander (*Persicaria odorata*), Wasabi (*Wasabia japonica*), Watercress, Wattleseed, Wild ginger, Wild Lettuce, Wild thyme, Winter savory, Witch Hazel, Wolfberry, Wood Avens, Wood Betony, Woodruff, Wormwood, Yarrow, Yerba Buena, Yohimbe, Za'atar, Zedoary Root.

Examples of fruits which can be treated according to the present invention are selected from the non-exhaustive enumeration of fruits consisting of banana, blackcurrant, redcurrant, gooseberry, tomato, eggplant, guava, lucuma, chili pepper, pomegranate, kiwifruit, grape, table grapes, pumpkin, gourd, cucumber, melon, orange, lemon, lime, grapefruit, banana, cranberry, blueberry, blackberry, raspberry, boysenberry, hedge apple, pineapple, fig, mulberry, apple, pear, apricot, peach, cherry, plum, nectarine, green bean, sunflower seed and strawberry.

Examples of vegetables which can be treated according to the present invention are selected from the non-exhaustive enumeration of vegetables consisting of flower buds, such as: broccoli, cauliflower, globe artichokes; seeds, such as sweetcorn also known as maize; leaves, such as kale, collard greens, spinach, beet greens, turnip greens, endive; leaf sheaths, such as leeks; buds, such as Brussels sprouts; stems of leaves, such as celery, rhubarb; stem of a plant when it is still a young shoot, such as asparagus, ginger; underground stem of a plant, also known as a tuber, such as potatoes, Jerusalem artichokes, sweet potato, yam; whole immature plants, such as bean sprouts; Roots, such as carrots, parsnips, beets, radishes, turnips; bulbs, such as onions, garlic, shallots.

In a preferred embodiment of the invention the succinate dehydrogenase inhibitors and/or the complex III inhibitor are applied to stone fruit such as apricots, cherries, almonds and peaches in order to improve the ratio of harmful to beneficial microorganisms. It has been found that the improved ratio leads to a significantly extended shelf life and storeability compared with untreated fruits.

The succinate dehydrogenase inhibitors and/or the complex III inhibitors, preferably fluopyram, can be employed for controlling fungal pathogens without impairing the content of beneficial microorganisms in crops within a certain period of time after treating the crops bearing the fruits or vegetables or after treating the fruits or vegetables itself. Generally, the succinate dehydrogenase inhibitor is applied to the crop or to its fruits or vegetables prior to the harvest, more preferably prior to the maturation of fruits and vegetables, most preferably during the plant and fruit growth prior to its contamination with the fungal pathogen.

Even if the succinate dehydrogenase inhibitor and/or the complex III inhibitor is applied to the crop in a pre-harvest interval the microflora on the surface of the harvested fruits is significantly improved in terms of increased beneficial and reduced harmful microorganisms.

The period of time within which fungal pathogens can be controlled generally extends from 1 hour to 6 months, preferably from 1 week to 1 month after the treatment of the crops or its fruits or vegetables with the active compounds.

When employing the succinate dehydrogenase inhibitors and/or the complex III inhibitor, preferably fluopyram and/or trifloxystrobin, according to the present invention for controlling fungal pathogens without impairing beneficial microorganisms, the application rates can be varied within a broad range, depending on the type of application. For foliar applications the application rates of active compound are generally ranging from 1 to 3000 g/ha, more preferably from 25 to 750 g/ha, most preferably from 30 to 500 g/ha based upon the pure a.s. (active substance).

According to the present invention, the succinate dehydrogenase inhibitor, preferably fluopyram, can be applied to all parts of the crops such as shoot, leaf, flower, root, leaves, needles, stalks, stems, flowers, vegetative buds and flower buds fruiting bodies and fruits.

Plants are understood as meaning, in the present context, all plants and plant populations, such as desired and undesired wild plants or crop plants (including naturally occurring crop plants). Crop plants or crops may be plants which can be obtained by conventional breeding and optimization methods or else by biotechnological and genetic engineering methods or by combinations of these methods, including the transgenic plants and including the plant varieties capable or not capable of being protected by plant breeders' rights.

According to the invention the treatment of the plants with the succinate dehydrogenase inhibitors and/or the complex III inhibitor, preferably fluopyram and/or trifloxystrobin is carried out directly by the customary treatment methods, for example by immersion, spraying, vaporizing, fogging, injecting, dripping, drenching, broadcasting or painting. In a preferred embodiment of the invention fluopyram is applied by injecting, dripping, drenching or spraying.

The succinate dehydrogenase inhibitors and/or complex III inhibitor, preferably fluopyram and/or trifloxystrobin, can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is liquid solvents, pressurized liquefied gases and/or solid carriers, optionally with the use of surface-active agents, that is emulsifiers and/or dispersants and/or foam formers. If the extender used is water, it is also possible to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants, for example, lignosulphite waste liquors and methylcellulose are suitable.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of the succinate dehydrogenase inhibitor, preferably between 0.5 and 90 percent by weight, based upon the total formulation.

According to the present invention, the succinate dehydrogenase inhibitors and/or complex III inhibitors, preferably fluopyram and/or trifloxystrobin, as such or their formulations, can also be used as a mixture with known fungicides, bactericides, acaricides, nematicides, or insecticides, for example, to broaden the activity spectrum or prevent the development of resistance. In many instances, synergistic effects are obtained, i.e. the activity of the mixture exceeds the activity of the individual components.

A further embodiment of the invention relates to the use of a composition comprising a succinate dehydrogenase inhibitor, preferably fluopyram, and a second fungicide for controlling fungal pathogens without impairing the content of beneficial microorganisms.

Suitable fungicides which can be used in combination with the succinate dehydrogenase inhibitor, preferably with fluopyram are selected from the group consisting of (1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl) cycloheptanol (129586-32-9), (1.61) methyl 1-(2,2-dimethyl-2,3-dihydro-1H-inden-1-yl)-1H-imidazole-5-carboxylate (111323-95-0), (1.62) N'-{5-(difluoromethyl)-2-methyl-4-[3-(trimethylsilyl)propoxy]phenyl}-N-ethyl-N-methyl imidoformamide, (1.63) N-ethyl-N-methyl-N'-{2-methyl-5-(trifluoromethyl)-4-[3-(trimethylsilyl)-propoxy] phenyl}imidoformamide and (1.64) O-[1-(4-methoxyphenoxy)-3,3-dimethylbutan-2-yl]1H-imidazole-1-carbothioate (111226-71-2).

(2) inhibitors of the respiratory chain at complex I or II, for example (2.1) bixafen (581809-46-03), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) furametpyr (123572-88-3), (2.9) furmecyclox (60568-05-0), (2.10) isopyrazam (mixture of syn-epimeric racemate 1RS,4SR,9RS and anti-epimeric racemate 1RS,4SR,9SR) (881685-58-1), (2.11) isopyrazam (anti-epimeric racemate 1RS,4SR,9SR), (2.12) isopyrazam (anti-epimeric enantiomer 1R,4S,9S), (2.13) isopyrazam (anti-epimeric enantiomer 1S,4R,9R), (2.14) isopyrazam (syn epimeric racemate 1RS,4SR,9RS), (2.15) isopyrazam (syn-epimeric enantiomer 1R,4S,9R), (2.16) isopyrazam (syn-epimeric enantiomer 1S,4R,9S), (2.17) mepronil (55814-41-0), (2.18) oxycarboxin (5259-88-1), (2.19) penflufen (494793-67-8), (2.20) penthiopyrad (183675-82-3), (2.21) sedaxane (874967-67-6), (2.22) thifluzamide (130000-40-7), (2.23) 1-methyl-N-[2-(1,1,2,2-tetrafluoroethoxy)phenyl]-3-(trifluoromethyl)-1H-pyrazole-4-carboxamide, (2.24) fluxapyroxad (907204-31-3), (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide and salts thereof.

(3) inhibitors of the respiratory chain at complex III, for example (3.1) amisulbrom (348635-87-0), (3.2) azoxystrobin (131860-33-8), (3.3) cyazofamid (120116-88-3), (3.4) dimoxystrobin (141600-52-4), (3.5) enestroburin (238410-11-2) (known from WO 2004/058723), (3.6) famoxadone (131807-57-3) (known from WO 2004/058723), (3.7) fenamidone (161326-34-7) (known from WO 2004/058723), (3.8) fluoxastrobin (361377-29-9) (known from WO 2004/058723), (3.9) kresoxim-methyl (143390-89-0) (known from WO 2004/058723), (3.10) metominostrobin (133408-50-1) (known from WO 2004/058723), (3.11) orysastrobin (189892-69-1) (known from WO 2004/058723), (3.12) picoxystrobin (117428-22-5) (known from WO 2004/058723), (3.13) pyraclostrobin (175013-18-0) (known from WO 2004/058723), (3.14) pyrametostrobin (915410-70-7) (known from WO 2004/058723), (3.15) pyraoxystrobin (862588-11-2) (known from WO 2004/058723), (3.16) pyribencarb (799247-52-2) (known from WO 2004/058723), (3.17) trifloxystrobin (141517-21-7) (known from WO 2004/058723), (3.18) (2E)-2-(2-{[6-(3-chloro-2-methylphenoxy)-5-fluoropyrimidin-4-yl] oxy}phenyl)-2-(methoxyimino)-N-methylethanamide (known from WO 2004/058723), (3.19) (2E)-2-(methoxyimino)-N-methyl-2-(2-{[({(1E)-1-[3-(trifluoromethyl)phenyl]ethylidene}amino)oxy]methyl}phenyl)ethanamide (known from WO 2004/058723) and salts thereof, (3.20) (2E)-2-(methoxyimino)-N-methyl-2-{2-[(E)-({1-[3-(trifluoromethyl)phenyl]-ethoxy}imino)methyl] phenyl}ethanamide (158169-73-4), (3.21) (2E)-2-{2-[({[(1E)-1-(3-{[(E)-1-fluoro-2-phenylethenyl]oxy}phenyl) ethylidene]amino}oxy)methyl]phenyl}-2-(methoxyimino)-N-methylethanamide (326896-28-0), (3.22) (2E)-2-{2-[({[(2E,3E)-4-(2,6-dichlorophenyl)but-3-en-2-ylidene] amino}oxy)methyl]-phenyl}-2-(methoxyimino)-N-methylethanamide, (3.23) 2-chloro-N-(1,1,3-trimethyl-2,3-dihydro-1H-inden-4-yl)pyridine-3-carboxamide (119899-14-8), (3.24) 5-methoxy-2-methyl-4-(2-{[({(1E)-1-[3-(trifluoromethyl)phenyl]ethylidene}amino)oxy] methyl}phenyl)-2,4-dihydro-3H-1,2,4-triazol-3-one, (3.25) methyl (2E)-2-{2-[({cyclopropyl[(4-methoxyphenyl)imino] methyl}sulfanyl)methyl]phenyl}-3-methoxyprop-2-enoate (149601-03-6), (3.26) N-(3-ethyl-3,5,5-trimethylcyclohexyl)-3-(formylamino)-2-hydroxybenzamide (226551-21-9), (3.27) 2-{2-[(2,5-dimethylphenoxy)methyl]phenyl}-2-methoxy-N-methylacetamide (173662-97-0), (3.28) (2R)-2-{2-[(2,5-dimethylphenoxy)methyl]phenyl}-2-methoxy-N-methylacetamide (394657-24-0) and salts thereof.

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluoro-phenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7) and salts thereof.

(5) Compounds capable to have a multisite action, like for example (5.1) bordeaux mixture (8011-63-0), (5.2) captafol (2425-06-1), (5.3) captan (133-06-2) (known from WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper(2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (2234562), (5.24) maneb (12427-38-2), (5.25) metiram (9006-42-2), (5.26) metiram zinc (9006-42-2), (5.27) oxine-copper (10380-28-6), (5.28)

propamidine (104-32-5), (5.29) propineb (12071-83-9), (5.30) sulphur and sulphur preparations including calcium polysulphide (7704-34-9), (5.31) thiram (137-26-8), (5.32) tolylfluanid (731-27-1), (5.33) zineb (12122-67-7), (5.34) ziram (137-30-4) and salts thereof.

(6) Compounds capable to induce a host defence, like for example (6.1) acibenzolar-S-methyl (135158-54-2), (6.2) isotianil (224049-04-1), (6.3) probenazole (27605-76-1) and (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7) and (7.7) pyrimethanil (53112-28-0).

(8) Inhibitors of the ATP production, for example (8.1) fentin acetate (900-95-8), (8.2) fentin chloride (639-58-7), (8.3) fentin hydroxide (76-87-9) and (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1) and (11.6) tricyclazole (41814-78-2).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, like for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds like for example (15.1) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.2) 1-(4-methoxyphenoxy)-3,3-dimethylbutan-2-yl 1H-imidazole-1-carboxylate (111227-17-9), (15.3) 2,3,5,6-tetrachloro-4-(methylsulfonyl)pyridine (13108-52-6), (15.4) 2,3-dibutyl-6-chlorothieno[2,3-d]pyrimidin-4(3H)-one (221451-58-7), (15.5) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.6) 2-butoxy-6-iodo-3-propyl-4H-chromen-4-one, (15.7) 2-phenylphenol and salts (90-43-7), (15.8) 3,4,5-trichloropyridine-2,6-dicarbonitrile (17824-85-0), (15.9) 3-[5-(4-chlorophenyl)-2,3-dimethyl-1,2-oxazolidin-3-yl]pyridine, (15.10) 3-chloro-5-(4-chlorophenyl)-4-(2,6-difluorophenyl)-6-methylpyridazine, (15.11) 4-(4-chlorophenyl)-5-(2,6-difluorophenyl)-3,6-dimethylpyridazine, (15.12) 5-amino-1,3,4-thiadiazole-2-thiol, (15.13) 5-chloro-N'-phenyl-N'-(prop-2-yn-1-yl)thiophene-2-sulfonohydrazide (134-31-6), (15.14) 5-methyl-6-octyl[1,2,4]triazolo[1,5-a]pyrimidin-7-amine, (15.15) ametoctradin (865318-97-4), (15.16) benthiazole (21564-17-0), (15.17) bethoxazin (163269-30-5), (15.18) capsimycin (70694-08-5), (15.19) carvone (99-49-0), (15.20) chinomethionat (2439-01-2), (15.21) chlazafenone (688046-61-9), (15.22) cufraneb (11096-18-7), (15.23) cyflufenamid (180409-60-3), (15.24) cynnoxanil (57966-95-7), (15.25) cyprosulfamide (221667-31-8), (15.26) dazomet (533-74-4), (15.27) debacarb (62732-91-6), (15.28) dichlorophen (97-23-4), (15.29) diclomezine (62865-36-5), (15.30) difenzoquat (43222-48-6), (15.31) difenzoquat methylsulphate (43222-48-6), (15.32) diphenylamine (122-39-4), (15.33) ecomate, (15.34) ethyl (2Z)-3-amino-2-cyano-3-phenylprop-2-enoate, (15.35) flumetover (154025-04-4), (15.36) fluoroimide (41205-21-4), (15.37) flusulfamide (106917-52-6), (15.38) flutianil (304900-25-2), (15.39) fosetyl-aluminium (39148-24-8), (15.40) fosetyl-calcium, (15.41) fosetyl-sodium (39148-16-8), (15.42) hexachlorobenzene (118-74-1), (15.43) irumamycin (81604-73-1), (15.44) methasulfocarb (66952-49-6), (15.45) methyl isothiocyanate (556-61-6), (15.46) metrafenone (220899-03-6), (15.47) mildiomycin (67527-71-3), (15.48) N-(4-chlorobenzyl)-3-[3-methoxy-4-(prop-2-yn-1-yloxy)phenyl]propanamide, (15.49) N-[(4-chlorophenyl)(cyano)methyl]-3-[3-methoxy-4-(prop-2-yn-1-yloxy)phenyl]propanamide, (15.50) N-[(5-bromo-3-chloropyridin-2-yl)methyl]-2,4-dichloropyridine-3-carboxamide, (15.51) N-[1-(5-bromo-3-chloropyridin-2-yl)ethyl]-2,4-dichloropyridine-3-carboxanide, (15.52) N-[1-(5-bromo-3-chloropyridin-2-yl)ethyl]-2-fluoro-4-iodopyridine-3-carboxamide, ° (15.53) N-{(E)-[(cyclopropylmethoxy)imino][6-(difluoromethoxy)-2,3-difluorophenyl]methyl}-2-phenylacetamide, (15.54) N-{(Z)-[(cyclopropylmethoxy)imino][6-(difluoromethoxy)-2,3-difluorophenyl]methyl}-2-phenylacetamide (221201-92-9), (15.55) natamycin (7681-93-8), (15.56) nickel dimethyldithiocarbamate (15521-65-0), (15.57) nitrothal-isopropyl (10552-74-6), (15.58) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.59) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.60) octhilinone (26530-20-1), (15.61) oxamocarb (917242-12-7), (15.62) oxyfenthiin (34407-87-9), (15.63) pentachlorophenol and salts (87-86-5), (15.64) pentyl {6-[({[(1-methyl-1H-tetrazol-5-yl)(phenyl)methylidene]amino}oxy)methyl]pyridin-2-yl}carbamate, (15.65) phenazine-1-carboxylic acid, (15.66) phenothrin, (15.67) phosphorous acid and its salts (13598-36-2), (15.68) propamocarb-fosetylate, (15.69) propanosine-sodium (88498-02-6), (15.70) proquinazid (189278-12-4), (15.71) pyrrolnitrin (1018-71-9) (known from EP-A 1 559 320), (15.72) quinolin-8-ol (134-31-6), (15.73) quinolin-8-ol sulfate (2:1) (134-31-6), (15.74) fenpyrazamine (473798-59-3), (15.75) tebufloquin (376645-78-2), (15.76) tecloftalam (76280-91-

6), (15.77) tolnifanide (304911-98-6), (15.78) triazoxide (72459-58-6), (15.79) trichlamide (70193-21-4), (15.80) zarilamid (84527-51-5) and salts thereof.
(16) Further compounds like for example (2.27) 1-methyl-3-(trifluoromethyl)-N-[2'-(trifluoromethyl)biphenyl-2-yl]-1H-pyrazole-4-carboxamide, (2.28) N-(4'-chlorobiphenyl-2-yl)-3-(difluoromethyl)-1-methyl-1H-pyrazole-4-carboxamide, (2.29) N-(2',4'-dichlorobiphenyl-2-yl)-3-(difluoromethyl)-1-methyl-1H-pyrazole-4-carboxamide, (2.30) 3-(duoromethyl)-1-methyl-N-[4'-(trifluoromethyl)biphenyl-2-yl]-1H-pyrazole-4-carboxamide, (2.31) N-(2',5'-difluorobiphenyl-2-yl)-1-methyl-3-(trifluoromethyl)-1H-pyrazole-4-carboxamide, (2.32) 3-(difluoromethyl)-1-methyl-N-[4'-(prop-1-yn-1-yl)biphenyl-2-yl]-1H-pyrazole-4-carboxamide (known from WO 2004/058723), (2.33) 5-fluoro-1,3-dimethyl-N-[4'-(prop-1-yn-1-yl)biphenyl-2-yl]-1H-pyrazole-4-carboxamide (known from WO 2004/058723), (2.34) 2-chloro-N-[4'-(prop-1-yn-1-yl)biphenyl-2-yl]pyridine-3-carboxamide (known from WO 2004/058723), (2.35) 3-(difluoromethyl)-N-[4'-(3,3-dimethylbut-1-yn-1-yl)biphenyl-2-yl]-1-methyl-1H-pyrazole-4-carboxamide (known from WO 2004/058723), (2.36) N-[4'-(3,3-dimethylbut-1-yn-1-yl)biphenyl-2-yl]-5-fluoro-1,3-dimethyl-1H-pyrazole-4-carboxamide (known from WO 2004/058723), (2.37) 3-(difluoromethyl)-N-(4'-ethynylbiphenyl-2-yl)-1-methyl-1H-pyrazole-4-carboxamide (known from WO 2004/058723), (2.38) N-(4'-ethynylbiphenyl-2-yl)-5-fluoro-1,3-dimethyl-1H-pyrazole-4-carboxamide (known from WO 2004/058723), (2.39) 2-chloro-N-(4'-ethynylbiphenyl-2-yl)pyridine-3-carboxamide (known from WO 2004/058723), (2.40) 2-chloro-N-[4'-(3,3-dimethylbut-1-yn-1-yl)biphenyl-2-yl]pyridine-3-carboxamide (known from WO 2004/058723), (2.41) 4-(difluoromethyl)-2-methyl-N-[4'-(trifluoro-methyl)biphenyl-2-yl]-1,3-thiazole-5-carboxamide (known from WO 2004/058723), (2.42) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (2.43) 2-chloro-N-[4'-(3-hydroxy-3-methylbut-1-yn-1-yl)biphenyl-2-yl]pyridine-3-carboxamide (known from WO 2004/058723), (2.44) 3-(difluoromethyl)-N-[4'-(3-methoxy-3-methylbut-1-yn-1-yl)biphenyl-2-yl]-1-methyl-1H-pyrazole-4-carboxamide (known from WO 2004/058723), (2.45) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (2.46) 2-chloro-N-[4'-(3-methoxy-3-methylbut-1-yn-1-yl)biphenyl-2-yl]pyridine-3-carboxamide (known from WO 2004/058723) and salts thereof, (15.81) (5-bromo-2-methoxy-4-methylpyridin-3-yl)(2,3,4-trimethoxy-6-methylphenyl)methanone (known from EP-A 1 559 320) and (9.10) N-[2-(4-{[3-(4-chlorophenyl)prop-2-yn-1-yl]oxy}-3-methoxyphenyl)ethyl]-N2-(methyl-sulfonyl)valinamide (220706-93-4).

In a preferred embodiment the second fungicide is trifloxystrobin. In a more preferred embodiment of the invention a composition comprising fluopyram and trifloxystrobin is used for controlling fungal pathogens, for instance *Botrytis* spp. and *Penicillium* spp. in stone fruits, such as cherries, nectarines, apricots and peaches.

In a further embodiment of the invention, it has been found that the pre-harvest or in season treatment of a succinate dehydrogenase inhibitor, preferably of fluopyram, increases the storability and/or the shelf life of the harvested fruits or vegetables.

Investigations carried out on harvested stone fruits which were obtain from crops treated with succinate dehydrogenase inhibitors and/or strobilurines prior to the harvest of the fruits have shown that the number of pathogen colonies was significantly reduced. In particular the presence of pathogens like *Botrytis* spp. and *Penicillium* spp. which both are the main pathogens causing post harvest problems, like of fruit rot, decreases. Likewise, the number of colonies of beneficial microorganisms, like pink yeast, white yeast, yellow yeast, *Bacillus* spp., *Epicoccum* spp., white bacteria, yellow bacteria, black bacteria, *Paecilomyces* spp., and *Ulocladium* spp. was significantly increased.

Thus, in a preferred embodiment the invention relates to the increase of *Paecilomyces* spp., *Ulocladium* spp., white and yellow yeasts and white and yellow bacteria in the surface microflora of fruits, preferably of stone fruits, such as peaches, nectarines and apricots, by in-season and/or preharvest application of compositions comprising fluopyram and trifloxystrobin.

In a most preferred embodiment the invention relates to the increase of yellow bacteria in the surface microflora of fruits, preferably of stone fruits, such as peaches, nectarines and apricots, by in-season and/or preharvest application of compositions comprising fluopyram and trifloxystrobin.

The present invention is exemplified by the following example.

EXAMPLES

Example: Stone Fruit Surface Microflora Reduction

Figure 1:
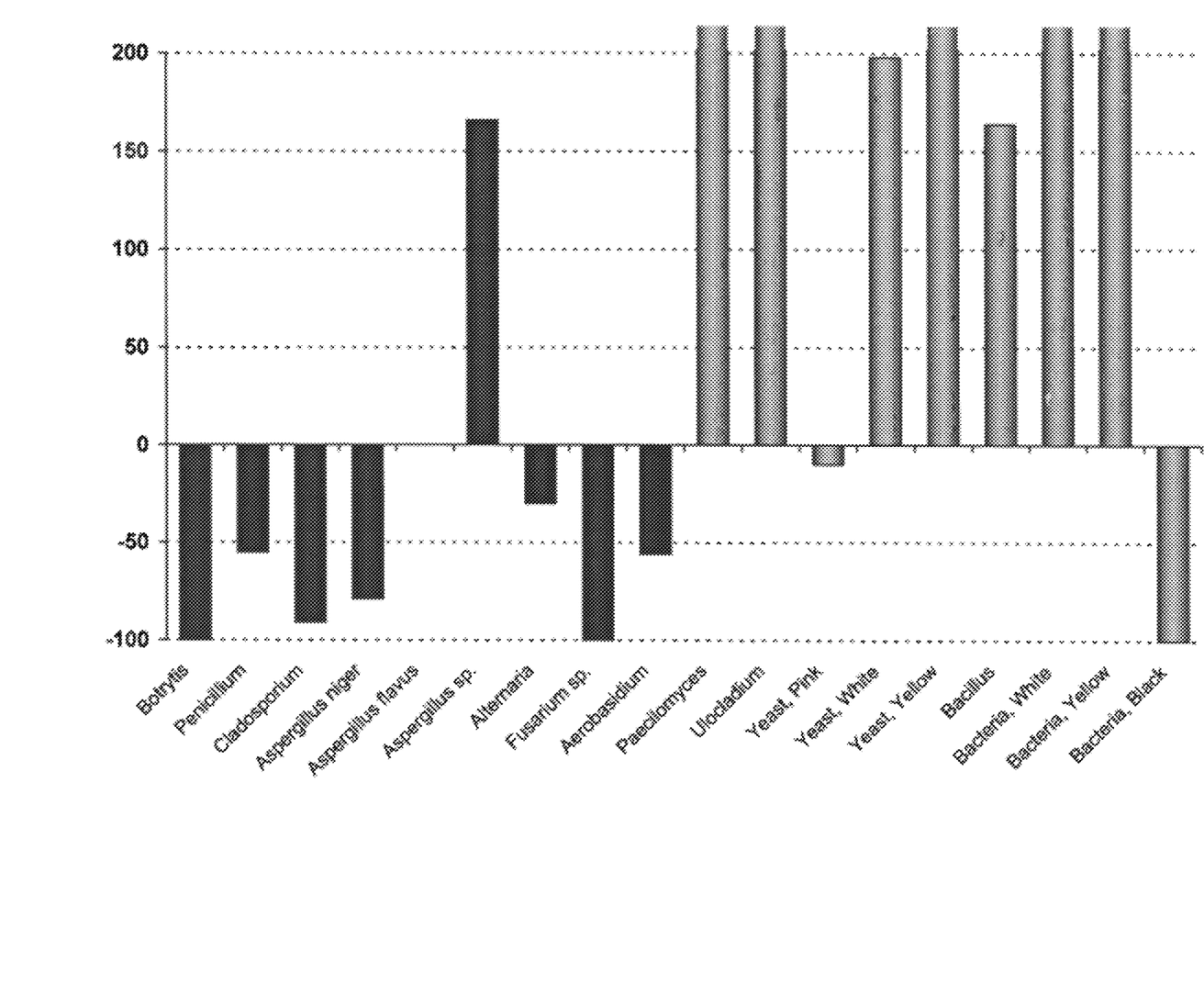
FIG. 1: demonstrates the percentual change of beneficial and harmful microorganisms in the surface microflora of stone fruits after a preharvest treatment with LUNA Sensation (SC 500 formulation of a mixture of fluopyram and trifloxystrobin in a 1:1 ratio).

The present example demonstrates the percentual change of beneficial and harmful microorganisms in the surface microflora of stone fruits after a preharvest treatment with LUNA Sensation (SC 500 formulation of a mixture of 21.4 wt.-% fluopyram and 21.4 wt.-% trifloxystrobin in a 1:1 ratio). Multiple applications were made from March-July in 935 liters per hectare with an air-blast sprayer, harvested fruit were washed, the wash was plated on selective media; and resulting colonies were enumerated.

TABLE 1

| Harmful/Undesired Microorganisms | |
|---|---|
| *Botrytis* | −100% |
| *Penicillium* | −55% |
| *Cladosporium* | −91% |
| *Aspergillus niger* | −79% |
| *Aspergillus flavus* | — |
| *Aspergillus* spp. | 166% |
| *Alternaria* | −30% |
| *Fusarium* spp. | −100% |
| *Aerobasidium* | −56% |
| Beneficial Microorganisms | |
| *Paecilomyces* | 680% |
| *Ulocladium* | 680% |
| Yeast, Pink | −10% |
| Yeast, White | 198% |
| Yeast, Yellow | 1460% |
| *Bacillus* | 164% |
| Bacteria, White | 322% |
| Bacteria, Yellow | 41620% |
| Bacteria, Black | −100% |

The present example demonstrates the percentual change of beneficial and harmful microorganisms in the surface microflora of stone fruits following a treatment program with LUNA Sensation (SC 500 formulation of a mixture of 21.4 wt.-% fluopyram and 21.4 wt. % trifloxystrobin in a 1:1 ratio). Multiple applications were made on a two-week interval from March-July in 935 liters per hectare with an air-blast sprayer, harvested fruit were washed, the wash was diluted in a range 1:1 to 1:1000 and plated on selective media; incubated, and resulting colonies were identified and enumerated as colony forming units per apricot 6 days later. The samples can be described as follow:

Pristine 38 WG:
Pristine containing 280 g ai/Ha (185 g/Ha boscalid and 94 g/Ha pyraclostrobin) was applied on dates: 6/3/10, 12/3/10, 2/4/10, 23/4/10, 14/5/10, 12/6/10, 3/7/10, 20/7/10, 13/8/10, 4/9/10, 25/9/10.

LS Early:
Luna Sensation 500 SC containing 183 g ai/Ha (91 g/Ha fluopyram and 91 g/Ha trifloxystrobin) was applied on dates: 6/3/10, 12/3/10, 2/4/10, 23/4/10, 14/5/10, 12/6/10.

LS Late:
Luna Sensation 500 containing 183 g ai/Ha (91 g/Ha fluopyram and 91 g/Ha trifloxystrobin) was applied on dates: 3/7/10, 20/7/10, 13/8/10, 4/9/10, 25/9/10

LS Full:
Luna Sensation 500 SC containing 183 g ai/Ha (91 g/Ha fluopyram and 91 g/Ha trifloxystrobin) was applied on dates: 6/3/10, 12/3/10, 2/4/10, 23/4/10, 14/5/10, 12/6/10, 3/7/10, 20/7/10, 13/8/10, 4/9/10, 25/9/10.

spp., *Cladosporium* spp., *Aspergillus niger*, *Alternaria* spp., *Fusarium* spp., *Aerobasidium* spp., Powdery Mildew Diseases, and combinations thereof.

2. The method of claim 1, wherein said Powdery Mildew Diseases comprise *Blumeria* diseases.

3. The method of claim 1, wherein the fluopyram, or the combination of fluopyram and trifloxystrobinm, is applied at an application rate of from 0.01 to 3 kg/ha based on the pure active ingredient.

4. The method of claim 1, wherein the fluopyram, or the combination of fluopyram and trifloxystrobin, is applied to the crop prior to the harvest of the fruits of the crop.

5. The method of claim 1, wherein the fluopyram, or the combination of fluopvram and trifloxvstrobin, is applied to the crop in combination with an additional fungicidally active compound.

6. The method of claim 3, wherein the fluopyram, or the combination of fluopyram and trifloxystrobin, is applied to the stone fruit crop for controlling *Botrytis* spp. and *Penicillium* spp. in cherries, nectarines, apricots or peaches.

7. The method of claim 1, wherein one or more of the harmful microorganisms cause Powdery Mildew Diseases.

TABLE 2

|  | Untreated | Untreated | LS early | LS early | LS full | LS full | Pristine | Pristine | LS late | LS late |
|---|---|---|---|---|---|---|---|---|---|---|
| Dilution | 1:1 | 1:1 | 1:1 | 1:1 | 1:1 | 1:1 | 1:1 | 1:1 | 1:1 | 1:1 |
| Aureobasidium | 212.5 | 335 | 530 | 242.5 | 542.5 | 607.5 | 767.5 | 105 | 315 | 272.5 |
| Rodtorula | 30.75 | 24.5 | 41.25 | 7.5 | 51.75 | 61.25 | 61.5 | 32.25 | 50.75 | 44.5 |
| Cladosporium | 28.75 | 28.5 | 30.25 | 1.25 | 14.75 | 34.5 | 35.25 | 10.75 | 33.5 | 11.75 |
| Alternaria | 0.5 | 1.75 | 1.75 | 0 | 1 | 0.75 | 1.25 | 1 | 0 | 1.25 |
| Botrytis | 0.75 | 0 | 0.25 | 0 | 0 | 0 | 0.25 | 0 | 0 | 0 |
| Coniothyrium | 0 | 1 | 0.25 | 0 | 0 | 0 | 0 | 0.25 | 0.5 | 0 |
| Penicillium | 0.5 | 1 | 2 | 0 | 0 | 0 | 0 | 0.25 | 0.5 | 0 |
| Monilinia | 0.25 | 0 | 0 | 0.25 | 0 | 0 | 0.25 | 0 | 0 | 0 |
| Fusarium | 0.75 | 1.25 | 0 | 0 | 1 | 0.25 | 0 | 0.5 | 1.25 | 0.5 |
| Rhizopus | 0 | 0 | 0 | 0 | 0 | 0 | 0 | 0 | 0.25 | 0 |
| A. flavus | 0 | 0.5 | 0 | 0 | 0 | 0 | 0 | 0 | 0 | 0 |
| A. niger | 0 | 0 | 0.75 | 0 | 0 | 0 | 0.25 | 0.25 | 0 | 0 |
| Epicoccum | 0.25 | 0 | 0 | 0 | 0 | 0 | 0 | 0.25 | 0 | 0 |
| Other Yeasts | 0 | 0 | 0 | 0 | 0.25 | 0.25 | 0 | 0 | 0 | 0.5 |
| Other & Unknown | 0.25 | 0.25 | 1.33 | 0.25 | 0.25 | 0 | 0 | 0 | 0 | 0.25 |

The invention claimed is:

1. A method for improving the ratio of beneficial to harmful microorganisms, on a stone fruit selected from the group consisting of apricot, cherry, peach and nectarine,
said method comprises applying 1 to 3,000 g/ha of fluopyram, or 1 to 3,000 g/ha of a combination of fluopyram and trifloxystrobin, to a stone fruit crop from which the stone fruit is obtained,
wherein the ratio of beneficial to harmful microorganisms on the stone fruit after said applying is higher than the ratio prior to said applying,
wherein the presence of a beneficial microorganism is not impaired or is increased and wherein the presence of a harmful microorganism is controlled, and
wherein said beneficial microorganisms are selected from the group consisting of pink yeast, white yeast, yellow yeast, *Bacillus* spp., *Epicoccum* spp., white bacteria, yellow bacteria, *Paecilomyces* spp., *Ulocladium* spp, and combinations thereof, and
said harmful microorganisms are selected from the group consisting of *Botrytis* spp, *Rhizopus* spp, *Penicillium*

8. The method of claim 1 wherein the fluopyram, or the combination of fluopyram and trifloxystrobin is applied at an application rate of from 0.025 to 0.75 kg/ha based on the pure active ingredients.

9. The method of claim 1 comprising administering fluopyram to the stone fruit.

10. The method of claim 1 wherein the content of the beneficial microorganisms after said application is twice or more than before said application, wherein the beneficial microorganisms are *Paecilomyces*, *Ulocladium*, White Yeast, Yellow Yeast, White Bacteria, Yellow Bacteria, or a combination thereof.

11. The method of claim 1 wherein the content of the beneficial microorganisms after said application is ten times more than before said application, wherein the beneficial microorganisms are Yellow Yeast, Yellow Bacteria, or a combination thereof.

12. The method of claim 1 wherein the ratio of fluopyram and trifloxystrobin in the combination is 1:1.

13. The method of claim 7 wherein the Powdery Mildew Diseases comprise *Blumeria* diseases.

14. The method of claim 1, wherein the method provides an increased shelf life of the stone fruit.

15. The method of claim 1, wherein the method controls the harmful microorganisms for from 1 hour to 6 months after the administration.

16. The method of claim 1, wherein the method controls the harmful microorganisms for from 1 week to 1 month after the administration.

17. The method of claim 1, wherein the stone fruit is apricot.

* * * * *